(12) United States Patent
Baube

(10) Patent No.: US 8,647,684 B2
(45) Date of Patent: Feb. 11, 2014

(54) PH MODIFIED INSECT REPELLENT/INSECTICIDE SOAP COMPOSED OF PLANT ESSENTIAL OILS

(76) Inventor: Howard Baube, Plymouth, MA (US)

( * ) Notice: Subject to any disclaimer, the term of this patent is extended or adjusted under 35 U.S.C. 154(b) by 0 days.

(21) Appl. No.: 13/363,540

(22) Filed: Feb. 1, 2012

(65) Prior Publication Data

US 2013/0196006 A1      Aug. 1, 2013

(51) Int. Cl.
   *A01N 65/00*   (2009.01)
(52) U.S. Cl.
   USPC .......................................... 424/725
(58) Field of Classification Search
   None
   See application file for complete search history.

(56) References Cited

U.S. PATENT DOCUMENTS

| | | |
|---|---|---|
| 4,671,960 A | 6/1987 | Thielen et al. |
| 4,707,496 A | 11/1987 | Simmons |
| 4,853,413 A | 8/1989 | Katz et al. |
| 5,320,066 A | 6/1994 | Gunter |
| 5,372,817 A | 12/1994 | Locke et al. |
| 5,466,710 A | 11/1995 | Weston et al. |
| 5,573,700 A | 11/1996 | Steltenkamp et al. |
| 5,776,477 A | 7/1998 | Ryder |
| 5,885,600 A | 3/1999 | Blum et al. |
| 6,231,865 B1 | 5/2001 | Hsu et al. |
| 6,395,765 B1 | 5/2002 | Etchegaray |
| 6,867,229 B2 | 3/2005 | Etchegaray |
| 7,144,591 B2 | 12/2006 | Bencsits |
| 7,575,765 B1 | 8/2009 | Hughes |
| 7,902,256 B2 | 3/2011 | Ping |

FOREIGN PATENT DOCUMENTS

| | | |
|---|---|---|
| CN | 1074334 A1 | 7/1993 |
| CN | 1081363 A1 | 2/1994 |
| EP | 0420520 A1 | 9/1990 |
| EP | 0736298 A1 | 10/1996 |
| EP | 0908171 A1 | 4/1999 |
| EP | 1880726 A1 | 1/2008 |
| JP | 2010138130 A2 | 6/2010 |
| WO | 9003730 A1 | 4/1990 |

OTHER PUBLICATIONS

Google Search 1 downloaded on Apr. 24, 2011 www.soapshed.com/store/bug-me-no-more-insect-repellent-soap-pr-16289.html.
Google Search 2 downloaded on Apr. 24, 2011 www.amazingsoap.com/bug-repellent.html.
Google Search 3 downloaded on Apr. 24, 2011 www.shop.birdsongstore.com/product.sc?categoryId=5&productId=20.
Google Search 4 downloaded on Apr. 24, 2011 www.onlynaturalpet.com/products/only-natural-pet-herbal-defense-spray/999034.aspx.

*Primary Examiner* — Michael Meller
(74) *Attorney, Agent, or Firm* — Russ Weinzimmer & Associates P.C.

(57) ABSTRACT

An insect repellent/insecticide starts with a main composition that is composed of the three primary essential oils of *eucalyptus, citronella*, and pine. A number of secondary essential oils can be added that provide additional beneficial characteristics, depending upon the application. A safe embedded tick "remove and kill" product includes a basic pH adjuster that is added to the main composition in an amount sufficient to adjust the pH of the main composition to approximately between 6.4 and 7.4, and preferably equal to about 6.5. A repellent spray dilutes the main composition in water to about 1% concentration by volume and a sufficient amount of a basic pH adjuster is added thereto to adjust the pH of the main composition to approximately between 6.4 and 7.4, and preferably equal to about 6.5. Soap includes the main composition combined with a detergent, glycerin, and a sufficient amount of an acidic pH adjuster to adjust the pH of the soap composition to approximately between 6.4 and 7.4, and preferably equal to about 6.8.

7 Claims, No Drawings

PH MODIFIED INSECT REPELLENT/INSECTICIDE SOAP COMPOSED OF PLANT ESSENTIAL OILS

FIELD OF THE INVENTION

This invention relates generally to insect repellents and insecticides, and more specifically to insect repellents and insecticides made of plant essential oils.

BACKGROUND OF THE INVENTION

Insects that require blood for reproduction (e.g. mosquitoes) and/or for further development during at least a portion of their life-cycle (e.g. fleas and ticks), are not only an annoyance to humans and animals, they are often the vectors of seriously debilitating and potentially fatal diseases to both humans and animals alike.

For example, tick-borne illnesses suffered by a host can result from infections by numerous types of pathogens, including bacteria, viruses, and protozoa. Because ticks can carry more than one type of pathogen simultaneously, hosts can actually be infected with more than one pathogen at the same time. This can make diagnosis and treatment even more complex. Notable tick-borne diseases include lyme disease, Rocky Mountain spotted fever, relapsing fever, tularemia, tick-borne meningoencephalitis, Colorado tick fever, Crimean-Congo hemorrhagic fever, babesiosis, cytauxzoonosis, ehrlichiosis, anaplasma, ehrlichia canis and candidatus neoehrlichia mikurensis. Tick bites can even create an allergy to red meat in some people, due to the allergen galactose alpha-1, 3-galactose.

Fleas can transmit a tapeworm called dipylidium caninum haemobartonellosis which affects red blood cells, another parasite called dipetalonema reconditum, plague caused by yersinia pestis, typhus caused by rickettsia typhi and rickettsia felis, tularemia caused by francisella tularensis and bartonella henselae, myxomatosis, the hymenolepiasis tapeworm, and trypanosome protozoans.

Mosquitoes in the United States can carry eastern equine encephalitis, western equine encephalitis, St. Louis encephalitis, La Crosse (LAC) encephalitis, West Nile Virus encephalitis, Dirofilaria immitis (heartworm), and sometimes even malaria.

Ticks are particularly insidious because they can spread disease while feeding during any of their life-cycle stages, which include their larva, nymph and adult stages. Ticks typically acquire the disease causing pathogens while feeding on the blood of an infected animal. This typically occurs during their nymph stage when they are more likely to feed on small disease-carrying animals such as rodents and birds. However, tick eggs can even become infected with pathogens inside of the ovaries of the adult female, meaning that baby ticks in the larva stage can be infectious immediately at birth and before feeding on their first host.

Ticks are particularly small when in the larva and nymph stages of their development, and this can make their presence very difficult to detect. They are also able to secrete small amounts of saliva with anesthetic properties so that the animal or person that is to serve as its host can't readily feel that the tick has broken the skin and has attached itself for a meal. Thus, they can often go unnoticed until they have completed their feeding, which can take up to several days.

The risk of acquiring a pathogen from a feeding tick increases commensurately with the amount the tick is allowed to feed. This is because as the tick completes its feeding, it tends to regurgitate some of its meal before releasing its grip on its host. This permits the back-flow of blood into the bloodstream of its host, which can include the pathogens. It is important to note that ticks can potentially be stimulated into disgorging some of their blood meal when they are disturbed during feeding. This can occur if the tick is squeezed or otherwise aggravated during an attempt to remove the tick, or in the presence of known formulations of repellents that the tick finds disturbing.

Thus, it is highly preferable that ticks, once attached and feeding, be removed as quickly and carefully as possible. It is critical that this be done without squeezing or otherwise disturbing or aggravating the tick into disgorging part of its meal, as this can greatly increase the possibility of being infected. Removing ticks while avoiding disturbing them can be extremely difficult, and preferably requires special tools to ensure that the tick is completely removed without leaving mouth parts embedded in the skin.

Clearly, the best way to thwart the spread of diseases from these insects is to discourage them from biting in the first place. For mosquitoes, this can be accomplished by using an effective repellent applied to the skin and/or clothing. Compositions based on the chemical known as DEET (N, N-diethyl-m-toluamide) can be applied to exposed skin for protection that lasts up to several hours. While DEET has been shown to be quite effective in repelling mosquitoes, its effectiveness in repelling ticks has not been well-demonstrated. Moreover, ticks are known to wander over the body of a potential host until one finds a suitable spot, perhaps where DEET has not been applied such as under clothing, or where it has worn off. The use of chemicals is often less than desirable. They can cause irritation to the skin of both humans and animals. DEET can also cause degradation of plastics and other synthetic materials because it is a fairly strong solvent.

A plethora of chemical-based flea and tick baths have also been developed and marketed that are designed to interfere with the brains and overall neurological systems of those insects, ultimately causing their death. Unfortunately, most of these products can also affect the neurological systems of animals and humans coming into contact therewith. Many of these chemicals are known carcinogens. For example, phenothrin (85.7%) in combination with methoprene was a popular topical flea/tick therapy for felines. Phenothrin kills adult fleas and ticks. Methoprene is an insect growth regulator that interrupts the insect's life cycle by killing the eggs. However, the U.S. Environmental Protection Agency required at least one manufacturer of these products to withdraw some products and has required strong cautionary statements to warn of adverse reactions on others.

A number of repellent/insecticide products have also been formulated using natural ingredients such as plant essential oils. A number of plant essential oils have demonstrated repellent properties on insects because the insects simply do not like how they smell. For example, lemon *eucalyptus* has reasonable repellent properties against mosquitoes. *Citronella* has been used in candles as a reasonably effective repellent. Fleas and ticks do not like the aroma of neem oil, cedarwood or cedar oil, and garlic. Peppermint oil, clove extract, neem oil, have also been shown to repel fleas and ticks, and can even kill them in the right concentrations.

One of the downsides to repellent/insecticide products made of plant essential oils is that they can be irritating to the skin of humans and animals alike. For example, when provided as a spray for application to the skin, they are typically diluted in water and are quite acidic in nature. The pH of such formulations can often be in the range of pH=3-4. When created as a soap or shampoo, the acidic nature of the essential oils are typically overwhelmed by the basic nature of the soap formulation and the pH of such formulations can be highly basic, in the range of pH=7.5 to 9. Thus, both of these product types as currently available on the market have a pH that is inadequate for effectiveness as a repellent/insecticidal, and that is poorly tolerated on the skin of humans and animals.

Another problem that is not well-addressed by currently available repellent/insecticides made from plant essential oils is that ticks can be aggravated by the application of such formulations once they are attached and feeding from a host. This can cause them to burrow into the skin even harder because they are not happy with the new environment created by applying the spray or soap, and may want to resist being extracted from the skin. Moreover, even if the applied formulation ultimately results in the tick's demise, as discussed above, it can potentially cause it to regurgitate some of its meal, thereby increasing the potential of spreading a disease from the tick.

SUMMARY OF THE INVENTION

An insect repellent/insecticide of the invention includes a main composition that is composed of the three primary essential oils of *eucalyptus, citronella* and pine to provide a primary insect repellent with insecticidal characteristics. A number of secondary essential oils (e.g. tea tree oil, rosemary oil, orange oil, chamomile, sage oil, lavender oil, peppermint oil and cedarwood oil) can be added that provide additional beneficial characteristics.

The main composition can be used to create a safe tick removal solution that includes the addition of basic pH adjuster (e.g. calcium carbonate, sodium bicarbonate, potassium bicarbonate, dolomite lime, oyster shells and egg shells) in an amount sufficient to adjust the pH of the main composition to approximately between 6.4 and 7.4, and preferably equal to about 6.5. This can be applied directly to an embedded tick, which voluntarily extricates itself from its host in response to the application and dies shortly thereafter.

The main composition can be combined with a liquid carrier such as distilled water or Isopropyl Alcohol (IPA) to about 1% concentration by volume to create an insect repellent and insecticide spray. A sufficient amount of a basic pH adjuster added to the main composition to adjust the pH of the spray to approximately between 6.4 and 7.4, and preferably equal to about 6.5.

The main composition can also be combined with a commercially available liquid detergent and glycerin to create an insect repellent and insecticide soap. A sufficient amount of an acidic pH adjuster (e.g. distilled white vinegar, apple cider vinegar, wine vinegar, lemon juice, lime juice, and citric acid) is added thereto to adjust the pH of the soap to approximately between 6.4 and 7.4, and preferably equal to about 6.8.

In an embodiment of the insecticide and insect repellent, a main composition can include *citronella* oil, *eucalyptus* oil and pine oil, to which a pH modifier is added in an amount sufficient to adjust the pH of the insecticide/repellent to a value of between 6.4 and 7.4. In another embodiment, the amount of the pH modifier is sufficient to adjust the pH of the insecticide/repellent to a value of substantially 6.5.

In a further embodiment, the main composition can include at least one essential oil additive selected from the group consisting of tea tree oil, rosemary oil, orange oil, chamomile oil, sage oil, lavender oil, peppermint oil and cedarwood oil, and the range of concentration of the additives selected from the list can range between 5% and 40% by volume of the main composition.

In further embodiments, the concentrations of *citronella* oil, *eucalyptus* oil and pine oil comprising the main composition are of substantially equal amounts by volume, or can have a ratio of concentrations falling substantially within the ranges of 0.5-2:0.5-2:0.5-2 respectively, or can have a ratio of concentrations substantially equal to 2:2:1 respectively.

In a further aspect of the invention, a 1-1.5% concentration by volume of the main composition can be combined with a 46-48% concentration by volume of glycerin and a 46-48% concentration by volume of a detergent, and a pH modifier added in an amount sufficient to create a soap having a pH value of between 6.4 and 7.4.

In other embodiments of the soap, at least one essential oil additive selected from the group consisting of tea tree oil, rosemary oil, orange oil, chamomile oil, sage oil, lavender oil, peppermint oil and cedarwood oil can be added to the main composition in amounts of between 5% and 40% by volume.

In still further aspects of the invention, 1-4% by volume of the main composition comprising *citronella, eucalyptus* oil, and pine oil can be added to 96-99% by volume of a liquid carrier, and a pH modifier to create a spray having a pH value of between 6.4 and 7.4. In further embodiments of the spray, at least one essential oil additive selected from the group consisting of tea tree oil, rosemary oil, orange oil, chamomile oil, sage oil, lavender oil, peppermint oil and cedarwood oil can be added to the main composition and in concentrations of between 5% and 40% by volume.

In further embodiments of the spray, the liquid carrier can be distilled water or Isopropyl Alcohol (IPA).

DETAILED DESCRIPTION OF THE INVENTION

Applicant's invention is a composition of matter that starts with a main composition that includes the essential oils of *eucalyptus, citronella*, and pine. These and all other additional essential oils specified below as constituents of embodiments of the main composition of the invention are commercially available from a number of reputable sources, such as New Directions Aromatics Inc., 6781 Columbus Road, Mississauga. L5T 2G9 Canada. Detailed information regarding each of these oils is supplied by New Directions Aromatics, (including their chemical constituents, methods of extraction, etc.), and is published in the form of data sheets that are available at the company's web site: www.newdirectionsaromatics.com. The data sheets for any of the essential oils set forth as constituents of any of the embodiments of the invention are hereby incorporated herein by reference.

In one embodiment of the main composition, the ratios of the concentrations of the primary constituent essential oils of *eucalyptus, citronella* and pine is substantially 2.5:2.5:1 respectively. In another embodiment of the main composition, the ratios of the concentrations of the primary constituent essential oils of *eucalyptus, citronella* and pine is substantially 1:1:1 respectively. In still another embodiment of the main composition, the ratios of the concentrations of the primary constituent essential oils of *eucalyptus, citronella* and pine is substantially fall within a range of 0.5-2:0.5-2:0.5-2 respectively.

In another embodiment of the main composition, concentration of the primary constituent essential oils of *eucalyptus, citronella* and pine is 25% by volume of *eucalyptus*, 25% by volume of *citronella* and 10% by volume of pine. In another embodiment of the main composition, the primary constituent essential oils of *eucalyptus, citronella* and pine can be of substantially equal parts, such as 20% each by volume. In still another embodiment of the main composition, the primary constituent essential oils of *eucalyptus, citronella* and pine can range between 10% and 25% by volume such that the combination of those constituents equals substantially 60% by volume of the main composition.

Each of the primary constituent essential oils has beneficial properties. For example, *citronella* oil has insect repellent as well as insecticidal and anti-fungal properties. *Eucalyptus* oil is used as an insect repellent and has biopesticide properties. *Eucalyptus* oil also has anti-inflammatory and analgesic qualities as a topically applied ingredient. Pine oil has deodorizing, antibacterial, antiseptic and disinfecting properties.

In another embodiment of the main composition of the invention, in addition to the primary constituent oils of *eucalyptus, citronella* and pine, any one or more of the following secondary essential oils may be added: tea tree oil, rosemary oil, orange oil, chamomile, sage oil, lavender oil, peppermint oil and cedarwood oil. In an embodiment of the main composition, the concentration of the primary constituent oils together equals substantially 60% of the volume off the main composition, and the concentration by volume of the secondary essential oils is substantially 40% of the volume of the main composition. In an embodiment of the main composition, each of the listed secondary essential oils is included at a concentration of about 5% by volume. In other embodiments, the concentrations of the various secondary essential oils can range between 0 and 15% by volume.

The secondary essential oils each have additional benefits to add to the effectiveness of any products made therewith. For example, chamomile oil contains azulin, which is known to be an anti-inflammatory agent. Tea tree oil has antimicrobial qualities including antiviral, antibacterial, antifungal, and antiseptic qualities. Orange oil has a pleasant aroma, is a mild solvent and has biopesticide properties. Rosemary oil has antioxident and anti-inflammatory properties. Cedarwood has insect repellent properties. Peppermint oil has natural pesticidal properties. Lavender oil and sage oil have been used to treat insect bites and stings.

The pH level of the main composition is highly acidic, and is typically in the range of pH=3.2 to 4.0. It has been observed that insect repellents and insecticides having such a highly acidic pH value, while possibly somewhat effective in repelling and/or killing fleas, ticks and/or mosquitoes, tend to be very irritating to the skin of both humans and animals. Moreover, they are not generally effective at causing easy and non-provocational removal of ticks that are already embedded within the skin of a human or an animal, which can potentially lead to disgorgement by the tick.

Thus, a number of practical formulations have been created that are far more effective because they are more gentle on the skin and because they lead to a calm and non-provocational detachment of embedded ticks. These formulations include a pH modifier that has been added to the formulation to bring the pH to a value of between 6.0 and 7.4. In another embodiment, the pH is substantially equal to 6.5.

A tick removing and killing formulation is ideal for removing and ultimately killing ticks that have become embedded within the skin, but without provoking the tick to disgorge any pathogens and without causing the tick to further embed itself against extraction, thereby requiring tweezers and a careful hand to remove. In an embodiment of the tick removing and killing composition, the main composition is combined with a basic pH modifier to adjust the pH to a value of substantially of between 6.4 and 7.4. The basic pH modifier can be any one or more of the following: calcium carbonate, sodium bicarbonate, potassium bicarbonate, dolomite lime, oyster shells and egg shells. In an embodiment, about 30 ml of the main composition having a pH of about 3.3 is combined with about 0.4 grams of sodium bicarbonate having a pH of about 7.8 to achieve a pH value of substantially 6.5 for the tick remover and killer composition.

The tick removing and killing composition can be applied directly to an embedded tick. The tick appears to absorb the composition without any apparent discomfort or aggravation, and without any attempts to further embed itself against possible extraction. Shortly thereafter the tick voluntarily disengages from its host without any apparent discomfort, aggravation or need for tweezers to pull the tick out by its head which can lead to dangerous disgorgement by the tick back into the bloodstream of its host. Shortly having removed itself from its host, the tick dies and can be simply discarded.

An embodiment of a spray repellent and insecticide composition used with the main composition also benefits from the addition of a basic pH adjuster to bring the pH value of the spray composition into a range of substantially between 6.4 and 7.4. This makes the spray ideal for use on the skin of both humans and animals as a repellent of ticks, fleas and mosquitoes, while not irritating the skin. The spray can also be used around the home on furniture, bedding, rugs, clothing and even in the garden without producing adverse effects on the environment or the surfaces on which it is sprayed.

The spray composition includes the addition of a liquid carrier such as water (preferably distilled) or Isopropyl Alcohol (IPA), to about 1-4% by volume of the main composition. Isopropyl Alcohol (IPA) can dry faster than water, which can be an advantage when applying to surfaces that preferably should not remain wet for an extended period of time. An amount of a basic pH adjuster (e.g. calcium carbonate, sodium bicarbonate, potassium bicarbonate, dolomite lime, oyster shells, and/or egg shells) is added to achieve the desired range of pH. In an embodiment of the spray repellent, approximately 2.5 ml of the main composition can be mixed with approximately 236 ml of water, and 0.8 grams of sodium bicarbonate to achieve a pH value of approximately 6.5.

An embodiment of a repellent and insecticide soap composition used with the main composition also benefits from the addition of a basic pH adjuster to bring the pH value of the spray composition into a range of substantially between 6.4 and 7.4. The pH adjuster can be, for example, distilled white vinegar, apple cider vinegar, wine vinegar, lemon juice, lime juice, and/or citric acid. This makes the soap ideal for use on the skin of both humans and animals as a repellent of ticks, fleas and mosquitoes, while being gentle on the skin. In an embodiment of the repellent soap and insecticide, approximately 0.5 ml of the main composition (pH=3.3) can be mixed with approximately 20 ml of Glycerin (pH=7.7), 20 ml of a commercially available liquid detergent (e.g. Joy liquid detergent made by Proctor & Gamble and having a pH=9.0), and an acidic pH modifier such as about 3.0 ml of white vinegar (pH=2.7). This will yield an embodiment of a repellent and insecticide soap composition having a pH of about 6.8.

The insect repellent/insecticide of the invention starts with a main composition that is composed of the three primary essential oils of *eucalyptus, citronella*, and pine to provide the primary insect repellent and insecticidal characteristics. A number of secondary essential oils (e.g. tea tree oil, rosemary oil, orange oil, chamomile, sage oil, lavender oil, peppermint oil, and cedarwood oil) can be added that provide additional beneficial characteristics.

To create a safe embedded tick "remove and kill" product, a basic pH adjuster (e.g. calcium carbonate, sodium bicarbonate, potassium bicarbonate, dolomite lime, oyster shells, and/or egg shells) is added to the main composition in an amount sufficient to adjust the pH of the main composition to approximately between 6.4 and 7.4, and preferably equal to about 6.5. This can be applied directly to an embedded tick, which voluntarily extricates itself from its host in response to the application and dies shortly thereafter.

To create a non-irritating repellent spray, the main composition is combined with a liquid carrier such as distilled water or Isopropyl Alcohol (IPA) (IPA) to about 1% concentration by volume and a sufficient amount of a basic pH adjuster is added thereto to adjust the pH of the main composition to approximately between 6.4 and 7.4, and preferably equal to about 6.5.

To create a non-irritating repellent/insecticidal soap, the main composition is combined with a commercially available liquid detergent, glycerin and a sufficient amount of an acidic pH adjuster (e.g. distilled white vinegar, apple cider vinegar, wine vinegar, lemon juice, lime juice, and/or citric acid) added thereto to adjust the pH of the soap composition to approximately between 6.4 and 7.4, and preferably equal to about 6.8.

It has been observed that the pine oil causes embedded ticks to more willingly absorb the main composition without apparent irritation or provocation to the tick, and to thereafter willingly release itself from the host before dying. It has also been observed that adjusting the pH to the range of between 6.4 and 7.4 not only provides the benefit of reducing irritation to the skin of animals and humans, but appears to further promote absorption of the essential oils by the embedded tick without causing it irritation or provoking it to embed itself further or to disgorge its meal while exposed to the constituents of the main composition.

While a pH of 6.5 to 6.8 appears to be ideal, the amount of pH adjustment can be varied within the specified range to accommodate the sensitivity of the skins of various animals.

What is claimed is:

1. An insecticide and insect repellent soap consisting essentially of:
    repellant and insecticide amounts of *citronella* oil, *eucalyptus* oil, and pine oil;
    glycerin;
    at least one detergent; and
    a pH modifier added in an amount sufficient to adjust the pH of the insecticide and insect repellent soap to a value of between 6.4 and 7.4.

2. The insecticide and insect repellent soap of claim 1, wherein the repellant and insecticide amounts of *citronella* oil, *eucalyptus* oil, and pine oil are together 1-4% by volume of said insecticide and insect repellent soap.

3. The insecticide and insect repellent soap of claim 1, wherein the glycerin is 46-50% by volume of said insecticide and insect repellent soap.

4. The insecticide and insect repellent soap of claim 1, wherein the pH modifier is selected from the group consisting of distilled white vinegar, apple cider vinegar, wine vinegar, lemon juice, and lime juice.

5. The insecticide and insect repellent soap of claim 1 wherein the *citronella* oil, *eucalyptus* oil, and pine oil have a ratio of concentrations falling substantially within the ranges of 0.5-2, 0.5-2, and 0.5-2, respectively.

6. An insecticide and insect repellent soap consisting essentially of:
    repellant and insecticide amounts of *citronella* oil, *eucalyptus* oil, and pine oil;
    glycerin;
    at least one detergent;
    at least one essential oil additive selected from the group consisting of: tea tree oil, rosemary oil, orange oil, chamomile oil, sage oil, lavender oil, peppermint oil, and cedarwood oil; and
    a pH modifier added in an amount sufficient to adjust the pH of the insecticide and insect repellent soap to a value of between 6.4 and 7.4.

7. The insecticide and insect repellent soap of claim 6 wherein the concentration of the at least one essential oil additive is substantially within a range of 0.5% to 1.6% by volume of the repellant and insecticide soap.

* * * * *